United States Patent [19]

Sinnott

[11] Patent Number: 5,246,452
[45] Date of Patent: Sep. 21, 1993

[54] VASCULAR GRAFT WITH REMOVABLE SHEATH

[75] Inventor: Joseph B. Sinnott, Chandler, Ariz.

[73] Assignee: Impra, Inc., Tempe, Ariz.

[21] Appl. No.: 867,332

[22] Filed: Apr. 13, 1992

[51] Int. Cl.⁵ ............................................. A61F 2/06
[52] U.S. Cl. .......................................... 623/1; 623/12
[58] Field of Search ............................ 623/1, 11, 12

[56] References Cited

U.S. PATENT DOCUMENTS

| | | | |
|---|---|---|---|
| 3,105,492 | 10/1963 | Jeckel | 623/1 |
| 4,321,711 | 3/1982 | Mano | 623/1 |
| 4,512,338 | 4/1985 | Balko et al. | 128/341 |
| 4,670,286 | 6/1987 | Nyilas et al. | 623/1 |
| 4,731,073 | 3/1988 | Robinson | 623/1 |
| 4,804,381 | 2/1989 | Turina et al. | 623/1 |
| 4,816,028 | 3/1989 | Kapadia et al. | 623/1 |
| 4,842,575 | 6/1989 | Hoffman, Jr. et al. | 623/1 |
| 4,850,999 | 7/1989 | Planck | 623/1 |
| 4,871,365 | 10/1989 | Dumican | 623/1 |

OTHER PUBLICATIONS

Jones et al., "A new sealant for knitted Dacron prostheses: Minimally cross-linked gelatin", *Journal of Vascular Surgery*, vol. 7, No. 3, Mar. 1988, pp. 414–419.
Harris et al. "An In Vitro Study of the Properties Influencing *Staphylococcus Epidermidis* Adhesion to Prosthetic Vascular Graft Materials", *Ann. Surg.*, Nov. 1987, pp. 612–620.

*Primary Examiner*—David Isabella
*Assistant Examiner*—Debra S. Brittingham
*Attorney, Agent, or Firm*—Cahill, Sutton & Thomas

[57] ABSTRACT

A porous graft is provided with a non-porous coating or sheath which does not adhere to the graft. After the graft is implanted into the patient, circulation is restored through the graft. The sheath is left in place temporarily while blood works its way through the wall of the porous graft to the non-porous sheath, where it is prevented from leaking. Clots form in the graft, sealing it. After a few minutes, the sheath is removed. The graft or the inside surface of the sheath can be pre-treated with a coagulant to accelerate clotting. The sheath is applied to the graft as a coating, e.g. by dipping or spraying, or as a separate sleeve, e.g. heat-shrinkable tubing. The sheath can be removed by cutting. Preferably, the sheath incorporates a string, strip, or ribbon of material which is attached to the sheath. For removal, the string is pulled, tearing the sheath which is removed with the string.

16 Claims, 2 Drawing Sheets

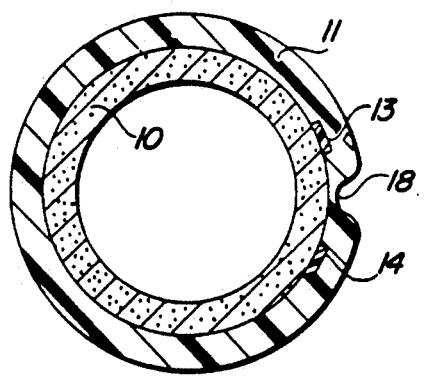
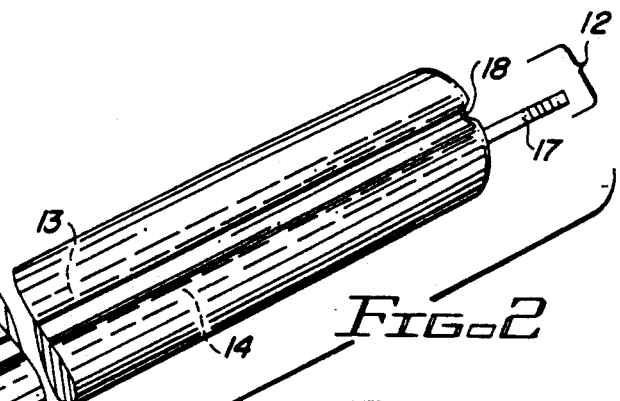
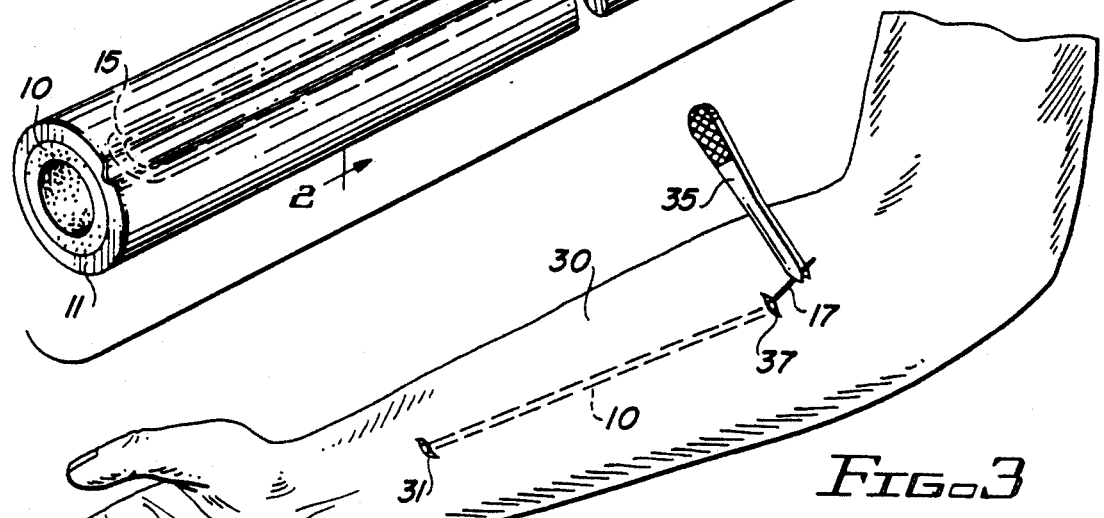
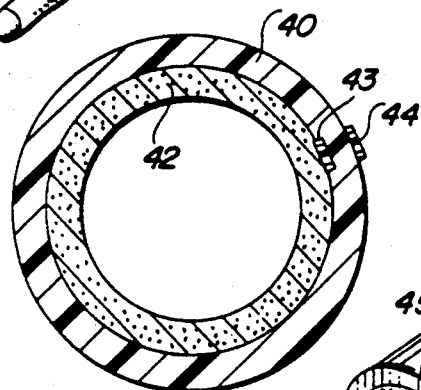
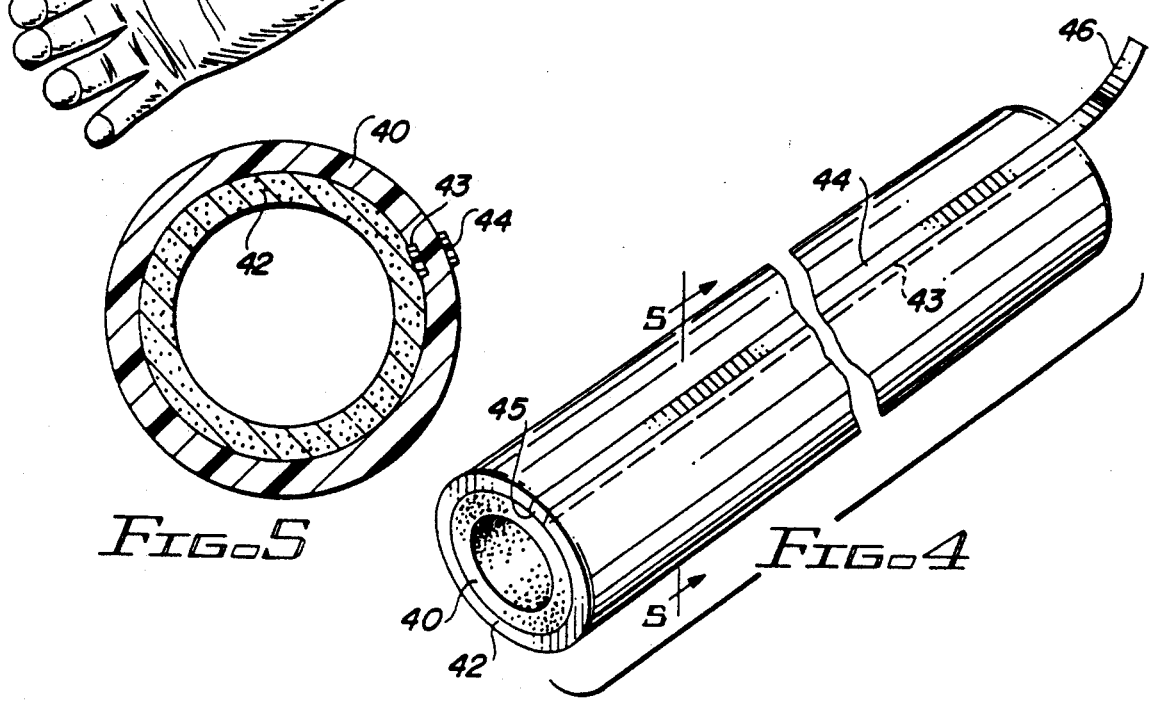

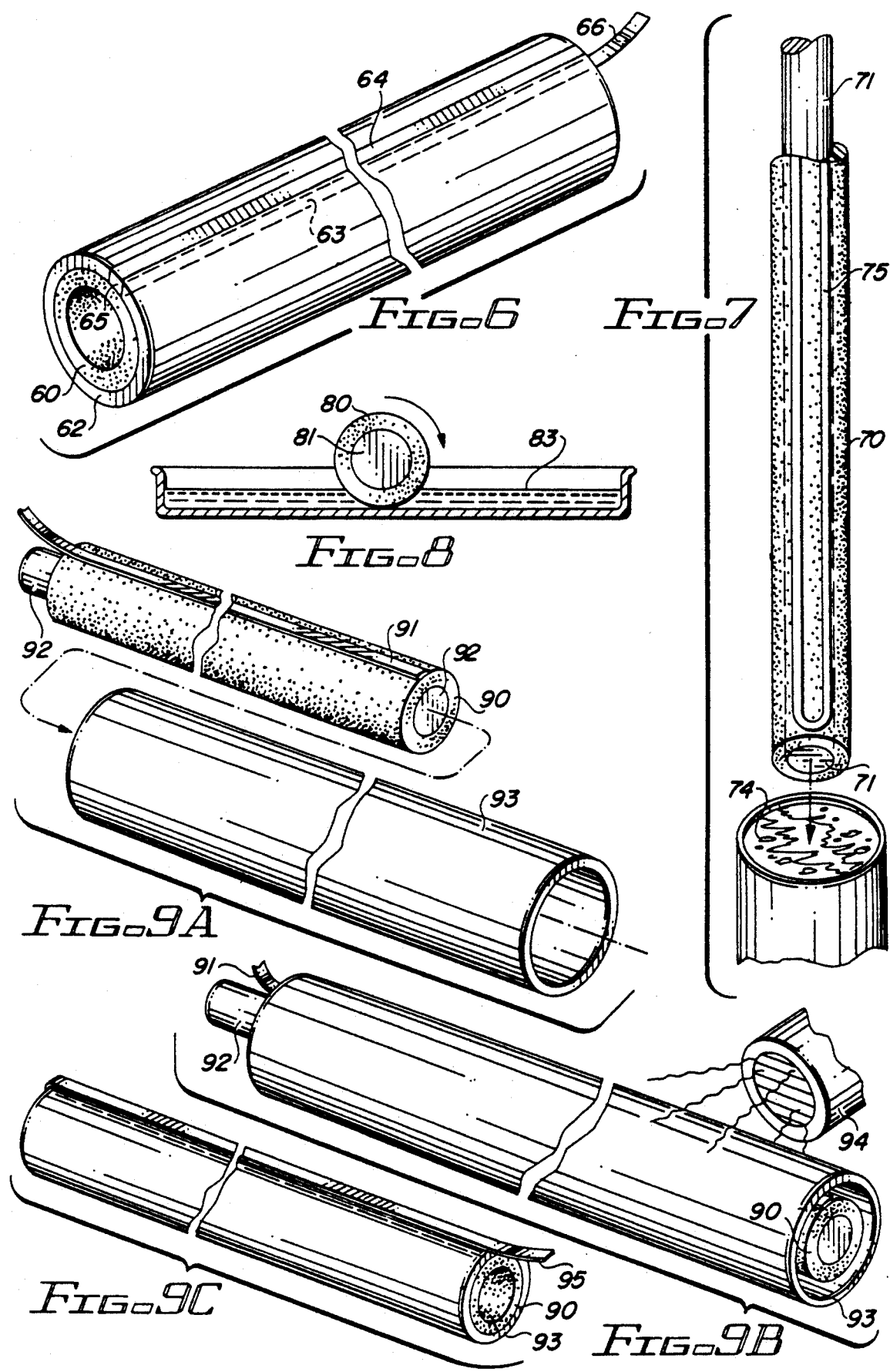

VASCULAR GRAFT WITH REMOVABLE SHEATH

BACKGROUND OF THE INVENTION

This invention relates to prosthetic grafts for implanting in the vascular system of patients and, in particular, to a porous vascular graft having a removable sheath.

Experiments in the early 1900's established venous and arterial autografting (replacing a section of a patient's blood vessel with a section of vein from elsewhere in the patient) as an effective technique for replacement of damaged or defective blood vessels. However, the need went beyond what could be treated by this technique, leading to a search for artificial or prosthetic veins and arteries for implanting in the vascular system. The need includes not only replacements for veins and arteries but also grafted blood vessels which can withstand repeated puncturing, e.g. for patients undergoing hemodialysis. By the 1950's, at least five characteristics of the ideal vascular graft were identified and became generally accepted. The graft must be pliable, durable, biocompatible, have minimum implantation porosity, and have maximum tissue porosity.

Generally "porosity" refers to whether or not the material is permeable by water. "Implantation porosity" refers to whether or not blood will leak through a graft when circulation is restored to the repaired vessel. "Tissue porosity" refers to the ability of cells from surrounding tissues to infiltrate the walls of the graft. The characteristics of the ideal graft are difficult to achieve simultaneously. Pliability, durability, and bio-compatibility can be achieved by proper choice of material. The last two of the five characteristics, relating to porosity, have proven the most difficult to achieve simultaneously. The porosity of a synthetic graft depends more upon how it was made than upon the material from which it was made.

At present there are three basic techniques for making vascular grafts: knitting, weaving, and stretching or expanding. Knitted or woven grafts are typically made from "Dacron" ® and expanded grafts are typically made from PTFE (polytetrafluorethylene or "Teflon" ®). Expanded PTFE has a microscopic structure of nodes interconnected by fibrils, and is normally impervious to water. PTFE can be made porous by greatly expanding it but is typically not porous.

There is a problem in that the graft with the greatest tissue porosity also has the greatest implant porosity, i.e. the graft which cells most easily infiltrate, thereby securely attaching the graft to the surrounding tissues, is also the graft which leaks the most blood when circulation is restored. Commercially available expanded grafts do not leak, woven grafts may or may not leak, and knitted grafts will leak. In general, the choice between knitted and woven grafts has been based upon proximity to the heart. More leakage is tolerated the further one is from the heart. Thus, woven grafts are generally used on or near the heart while knitted grafts are generally used away from the heart. The choice between porous and PTFE grafts is generally based upon the more rapid healing with porous grafts versus not having to pre-clot PTFE grafts and the better performance of PTFE grafts in smaller diameters.

Porous grafts, and very porous PTFE grafts, have a disadvantage in the need to control their porosity temporarily at the time of implantation; specifically, to minimize their implantation porosity to reduce leakage. Typically, the graft, which may have been pre-treated with coagulant, is soaked in the patient's blood to form clots in the graft, thereby sealing it. Pre-clotting decreases the pliability of the graft, interrupts the surgery, and extends the surgical time of the patient, all of which are significant disadvantages.

To avoid affecting surgical time, manufacturers of grafts have taken a renewed interest in pre-coated grafts; Cf. Jones et al., "A new sealant for knitted Dacron prostheses: Minimally cross-linked gelatin", *Journal of Vascular Surgery*, Vol. 7, No. 3, Mar. 1988, pages 414–419. Grafts have been pre-coated with soluble collagen (gelatin), insoluble collagen, albumin, and fibrin, all of which noticeably stiffen the graft. Because the coating stiffens the graft and relies on cell infiltration to re-absorb the coating material, a coating is usually applied only to knitted grafts. Woven grafts, which are already somewhat stiff, are usually not coated by commercial manufacturers.

Coating knitted grafts with organic material raises questions about the purity of the material and the contamination of the graft. The question of contamination has already been raised in connection with uncoated grafts; see, for example, Harris et al. "An In Vitro Study of the Properties Influencing *Staphylococcus Epidermidis* Adhesion to Prosthetic Vascular Graft Materials", *Ann. Surg.*, November 1987, pages 612–620. This article suggests that a silicone coating reduces the adherence of the S. E. bacterium.

Instead of, or in addition to, coatings, it has also been proposed to use multi-layer grafts of different materials. U.S. Pat. No. 3,105,492 discloses concentric knitted and woven tubes and asserts that this combination need not be externally pre-clotted. U.S. Pat. No. 4,850,999 discloses a knit tube within a braided hose or a PTFE tube within a braided hose. U.S. Pat. No. 4,871,365 discloses a graft having a non-absorbable layer surrounding an absorbable layer, held together by stitches, glue, or frictional contact.

In view of the foregoing, it is therefore an object of the invention to provide a vascular graft which does not require pre-clotting outside the patient.

Another object of the invention is to provide a mechanism for temporarily controlling the porosity of a vascular graft.

A further object of the invention is to render porous vascular grafts non-porous during implantation without decreasing the tissue porosity of the graft.

Another object of the invention is to provide a vascular graft with a non-porous sheath which is easily removed after the graft is surgically implanted.

A further object of the invention is to provide a vascular graft with a sheath which can be removed from a single end, without the need for access to the entire graft.

SUMMARY OF THE INVENTION

The foregoing objects are achieved in the invention in which a porous graft is provided with a non-porous coating or sheath which does not adhere to the graft. After the graft is implanted in the patient, circulation is restored through the graft. The sheath is left in place temporarily while blood works its way through the wall of the porous graft to the non-porous sheath, where it is prevented from leaking. Clots form in the graft, sealing it. After a few minutes, the sheath is removed. If necessary, e.g. when the patient is receiving an anti-coagulant, the graft is treated with a coagulant to accelerate clotting. The sheath is applied to the graft as a coating, e.g. by dipping or spraying, or as a separate sleeve, e.g. heat-shrinkable tubing. The sheath can be removed by cutting. Preferably, the sheath incorporates a string or ribbon of material which is attached to the sheath. For removal, the string is pulled, tearing the sheath which is removed with the string.

BRIEF DESCRIPTION OF DRAWINGS

A more complete understanding of the invention can be obtained by considering the following detailed description in conjunction with the accompanying drawings in which:

FIG. 1 is a cross-section of a graft constructed in accordance with a preferred embodiment of the invention.

FIG. 2 is a perspective view of the graft shown in FIG. 1.

FIG. 3 illustrates the removal of the coating through a single, small incision.

FIG. 4 illustrates the end portion of a coated graft constructed in accordance with an alternative embodiment of the invention.

FIG. 5 is a cross-section of the graft shown in FIG. 4.

FIG. 6 illustrates the end portion of a coated graft constructed in accordance with another alternative embodiment of the invention.

FIG. 7 illustrates the formation of the coating by endwise dipping.

FIG. 8 illustrates the formation of the coating by edgewise dipping or rolling.

FIGS. 9A, 9B, and 9C illustrate the steps in forming a coating from heat-shrinkable tubing.

DETAILED DESCRIPTION

FIGS. 1 and 2 illustrate a vascular graft and sheath as concentric tubes. The tubes do not have the same porosity. Specifically, graft 10 can be any porous graft such as knitted or loosely woven Dacron ® or highly expanded PTFE. Surrounding graft 10 is non-porous sheath 11 which can frictionally engage graft 10 but is otherwise not attached to it.

In a surgical operation, the graft need not be pre-clotted but can be implanted in the patient and sutured to the free ends of the vein or artery being repaired. The graft and sheath can be readily manipulated since the sheath is relatively thin, e.g. 0.5–5 mils thick, and does not significantly change the handling or flexibility of the graft. After the graft is attached, circulation is restored so that blood can flow down the length of the graft. Blood also works its way radially outward through the wall of graft 10, but is stopped by sheath 11 from leaking out of the graft, except perhaps at the suture holes. Within a few minutes, the blood clots within graft 10, sealing it.

If the patient had been given an anti-coagulant, such as heparin, the graft or the inside surface of the sheath can be pre-treated with coagulant. This is not the same as pre-clotting since the pre-treatment can be carried out prior to the operation rather than during the operation. Similarly, although one is waiting for the blood to clot in graft 10 the patient is not merely lying open. Circulation has been restored and ancillary procedures can be carried out.

After the graft is sealed, sheath 11 can be removed by the surgeon, e.g. by cutting along the length thereof. This requires access to the entire length of the graft. In many procedures, it is not necessary or desirable to have a large incision. It would be preferable to be able to remove the sheath from a single, small incision at one end of the graft.

The mechanism for doing this is also shown in FIGS. 1 and 2. Interposed between graft 10 and sheath 11 is release 12, preferably in the form of an elongated, U-shaped or open loop having both ends adjacent one end of the graft. Legs 13 and 14 are interconnected by curve 15 and extend the length of graft 10. The free end of at least one leg preferably extends past the end of the graft, such as end 17 on leg 14, so that the surgeon can readily grasp the release. If desired, the free ends of both legs can extend past the end of the graft.

Release 12 is attached to sheath 11 along at least one leg. Thus, as the surgeon pulls on end 17, the sheath tears along its length and is pulled off of graft 10. Although illustrated as parallel and extending straight from one end of graft 10 to the other, legs 13 and 14 need not be parallel nor straight. They could, for example, follow a helical path, either partially or completely around graft 10.

Release 12 is particularly useful in the procedure noted above and illustrated in FIG. 3 wherein a graft is inserted through a small incision and tunnelled under the skin to a second incision spaced from the first incision. Thus, the surgeon does not have access to the entire length of the graft after insertion. FIG. 3 illustrates the forearm of a person receiving a vein graft, e.g. to provide a vessel which can be repeatedly punctured for hemodialysis. Incisions 31 and 32 are made at separate locations in forearm 30 and graft 10, with sheath 11, is inserted through one incision and extended to the other incision. The ends of the graft are attached to the vein as appropriate and circulation is restored. After the blood has had a chance to soak into graft 10 and coagulate, sheath 11 is removed by grasping end 17 with forceps 35 and pulling gently. Release 12 tears sheath 11 and is removed, with sheath 11, through incision 32. Thus, only small incisions are used, circulation is restored quickly, and trauma to the patient is minimized.

Sheath 11 can comprise any suitable, non-porous material which will not adhere to graft 10, preferably a thin layer of material so that it is easily torn. Tearing can be enhanced by deforming the layer slightly, as shown by thinned strip 18 in FIG. 1. This assures tearing along strip 18. Preferred materials for sheath 11, largely because of their familiarity to users of grafts of the prior art, are polyethylene and PTFE, having a thickness of 0.5–5 mils. Any material which is pliable, durable, and bio-compatible can be used. Release 12 can comprise any suitable inelastic ribbon or cord such as polypropylene, cellophane ribbon, Nylon ® filament or PTFE filament, having a tear strength greater than that of the sheath. Release 12 is bonded to sheath 11 by heat o chemical adhesive such as cyanoacrylate.

FIGS. 4 and 5 illustrate an alternative embodiment of the invention in which porous graft 40 is surrounded by non-porous sheath 42. Unlike the embodiment of FIGS. 1 and 2, the release is only partially contained between graft 40 and sheath 42. Leg 43 of the release is between graft 40 and sheath 42 while leg 43 overlies sheath 42. Leg 43 is attached to sheath 42, while leg 44 need not be attached, although it can be tacked to the end of the sheath for the convenience of the surgeon. Leg 43 tears through the sheath as end 46 is drawn away from the graft. Curved portion 45 connects the legs together and initiates the tearing.

FIG. 6 illustrates a structure similar to that of FIG. 4, except that free end 66 is part of the leg between graft 60 and sheath 62. Leg 64 is attached to the outside of sheath 60 and tears through the sheath as end 66 is drawn away from the graft.

There are several methods for forming the sheath about the graft. In FIG. 7, graft 70 is mounted on vertical mandrel 71 and immersed in viscous liquid 74. Release 75 is tacked to the outer surface of graft 70 and is also immersed in the liquid, becoming attached to the sheath.

Liquid 74 can comprise any suitable material, such as silicone elastomer, which does not bond to graft 70. Unlike the 27% silicone solution described in the *Ann. Surg.* article, infra., liquid 74 is preferably a silicone elastomer, which is more viscous than the silicone solution, so that only the outer surface of the graft is coated in a continuous, non-porous layer. With a 27% silicone solution, individual fibers are coated and the graft remains porous, as described in the article.

The thickness of the coating that forms the sheath and the degree to which it penetrates the graft are determined by the duration of the immersion and the viscosity of the liquid. The appropriate viscosity varies with the porosity of the graft and is readily determined empirically. Viscosity can be controlled by temperature or diluents. Other coatings, such as polyurethane, can be used instead of silicone.

The coating must not form on the inside or lumina of graft 70. Mandrel 71 fills the interior of graft 70 to prevent this. The liquid must not enter from the ends of the graft, but form a coating only on the outer surface of the graft.

To assure or enhance the uniformity of the coating, it is preferred that the curing or drying of the coating be accelerated, e.g. by heating or the use of UV curable silicone coating material. Uniformity can be measured both radially (around any given diameter of the graft) or longitudinally (end to end). The embodiment of FIG. 7 simplifies obtaining radial uniformity since the mandrel is vertical.

The embodiment of FIG. 8 simplifies obtaining longitudinal uniformity since the mandrel is horizontal and the graft is rolled across the surface of the liquid in order to apply the coating. Specifically, graft 80 is mounted on mandrel 81, which rotates to immerse the outer surface of graft 80 in liquid 83. Liquid 83 is as described above. The advantage to this technique is that it avoids exposing the ends of the graft to the liquid. If the liquid is shallow enough, the mandrel can be eliminated and graft 80 is rolled across the bottom of container 84. A reciprocating rolling motion can be used to form longitudinal strip 18 (FIG. 1).

FIGS. 9A, 9B, and 9C illustrate the steps for attaching a heat shrinkable tube to a graft. Graft 90, and release 91, are mounted on mandrel 92 and inserted into tube 93. Heat is applied from a suitable heat source 94 and the tubing shrinks about graft 90, but does not attach to it. It is held in place by friction. As shown in FIG. 9C, the long leg of release 95 is brought back over the top of sheath 93 and tacked in place. The appliance is now ready for use. Suitable heat shrinkable materials include Teflon ®, polyolefin, and polyvinylchloride (PVC).

If it were desired for the interior of the grafts of FIGS. 7-9C to be pre-coated with coagulant, this is most easily accomplished by coating the mandrel with coagulant just prior to inserting it into the graft.

The invention thus provides a porous vascular graft which does not require pre-clotting outside the patient, yet temporarily controls the porosity of the graft. A non-porous sheath renders the graft temporarily non-porous during implantation without decreasing the tissue porosity of the graft. The non-porous sheath can be removed from a single end, without the need for access to the entire graft.

Having thus described several embodiments of the invention, it will be apparent to those of skill in the art that various modifications can be made within the scope of the invention. For example, the sheath can also be applied by spraying a coating onto the graft. While shown and described in conjunction with smooth, cylindrical grafts, it is understood that the invention includes corrugated or formed grafts as well. Tearing can be enhanced by any suitable means, e.g. thinning, as described above, or perforations.

I claim:
1. A vascular graft comprising:
   a tube or porous material, for attachment to a blood vessel said tube having a first end and a second end and a predetermined length between said first end and said second end;
   a removable sheath of non-porous material surrounding said tube for rendering said graft temporarily non-porous until blood working its way radially outward through said tube clots and seals said tube; and
   an elongated, open loop of inelastic material for removing said sheath after said tube is sealed by the blood, wherein said loop
      (i) extends along said length and
      (ii) at least a portion of said loop is contained between said tube and said sheath whereby said sheath is torn along its length when said loop is pulled.
2. The graft as set forth in claim 1 wherein said tube comprises woven Dacron brand synthetic fiber.
3. The graft as set forth in claim 1 wherein said tube comprises knitted Dacron brand synthetic fiber.
4. The graft as set forth in claim 1 wherein said tube comprises expanded PTFE.
5. The graft as set forth in claim 1 wherein a first portion of said loop underlies said sheath and a second portion of said loop overlies said sheath.
6. The graft as set forth in claim 1 wherein
   said loop has two free ends adjacent said first end; and
   one of said free ends extends a predetermined distance beyond said first end.
7. The graft as set forth in claim 1 wherein said tube contains coagulant.
8. The graft as set forth in claim 1 wherein said sheath comprises a tube of heat shrinkable material n contact with said tube of porous material.
9. A vascular graft having concentric inner and outer tubes of different porosity, said graft characterized in that
   an inelastic strip is between the inner and outer tubes and is attached to said outer tube for tearing the outer tube and removing the outer tube from the inner tube, whereby after said graft is attached to a blood vessel, blood working its way radially outward through said inner tube is stopped by said outer tube, the blood sealing said inner tube by clotting, whereafter said outer tube can be removed by pulling on said inelastic strip causing said outer tube to be torn along its length.

10. The vascular graft as set forth in claim 9 wherein said graft has two ends separated by a predetermined length and said inelastic strip extends along said length.

11. The vascular graft as set forth in claim 9 wherein said inelastic strip has a U-shape and two free ends adjacent one of said ends of said graft.

12. A vascular graft having concentric inner and outer tubes of predetermined length and different porosity, said graft characterized in that
said inner tube is porous;
said outer tube is a non-porous, removable sheath 0.5–5 mils thick; and
said graft includes an elongated strip of inelastic material attached to said outer tube for removing said outer tube from said inner tube, whereby after said graft is attached to a blood vessel, blood working its way radially outward through said inner tube is stopped by said outer tube, the blood sealing said inner tube by clotting, whereafter said outer tube can be removed by pulling on said inelastic strip causing said outer tube to be torn along its length.

13. The vascular graft as set forth in claim 12 wherein said outer tube is deformed along said length to facilitate tearing by said strip.

14. The vascular graft as set forth in claim 13 wherein said outer tube is perforated along said length.

15. The vascular graft as set forth in claim 14 wherein said outer tube has a reduced thickness portion extending said length.

16. The vascular graft as set forth in claim 12 wherein said outer tube is a coating on said inner tube.

* * * * *